(12) United States Patent
Kalfon

(10) Patent No.: US 10,327,938 B1
(45) Date of Patent: Jun. 25, 2019

(54) INTESTINAL SLEEVE

(71) Applicant: Allium Medical Solutions LTD., Caesarea Industrial Park South (IL)

(72) Inventor: Ziv Kalfon, Ein Hod (IL)

(73) Assignee: Allium Medical Solutions LTD., Ceasarea Industrial Park South (IL)

( * ) Notice: Subject to any disclaimer, the term of this patent is extended or adjusted under 35 U.S.C. 154(b) by 0 days.

(21) Appl. No.: 15/986,884

(22) Filed: May 23, 2018

(51) Int. Cl.
*A61F 2/04* (2013.01)
*A61F 5/00* (2006.01)

(52) U.S. Cl.
CPC ............ *A61F 5/0076* (2013.01); *A61F 2/04* (2013.01); *A61F 2002/045* (2013.01); *A61F 2230/0069* (2013.01)

(58) Field of Classification Search
CPC .... A61F 2002/045; A61F 2/04; A61F 5/0076; A61F 5/0036
See application file for complete search history.

(56) References Cited

U.S. PATENT DOCUMENTS

| | | |
|---|---|---|
| 7,682,330 B2 | 3/2010 | Meade et al. |
| 8,855,770 B2 | 10/2014 | Gross et al. |
| 8,888,732 B2 | 11/2014 | Raven et al. |
| 8,956,380 B2 | 2/2015 | Dominguez et al. |
| 9,011,365 B2 | 4/2015 | Connor |
| 9,173,734 B2 | 11/2015 | Vargas |
| 9,289,580 B2 | 3/2016 | Coleman |
| 9,463,107 B2 | 10/2016 | Babkes et al. |
| 9,504,591 B2 | 11/2016 | Burnett et al. |
| 9,681,974 B2 | 6/2017 | Dominguez et al. |
| 9,717,584 B2 | 8/2017 | Cully et al. |
| 2003/0114803 A1 | 6/2003 | Lerner |
| 2012/0232459 A1 | 9/2012 | Dann et al. |
| 2014/0316265 A1 | 10/2014 | Levin et al. |
| 2017/0181877 A1 | 6/2017 | Binmoeller |

*Primary Examiner* — Leslie R Deak
(74) *Attorney, Agent, or Firm* — Manelli Selter PLLC; Edward J. Stemberger

(57) ABSTRACT

A sleeve that is inserted into intestine has an extendable length, varying length. When no food is ingested the sleeve is short. The length of the sleeve could be thirty or less centimeter. When food is ingested the sleeve extends into the intestine the full length and reduces absorption of food by the intestine.

15 Claims, 5 Drawing Sheets

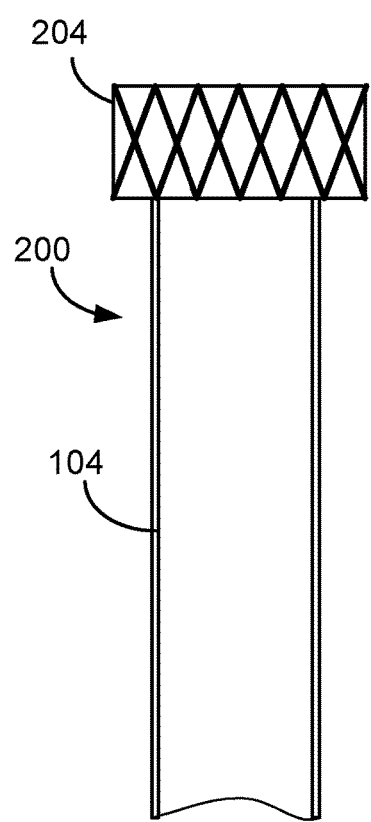
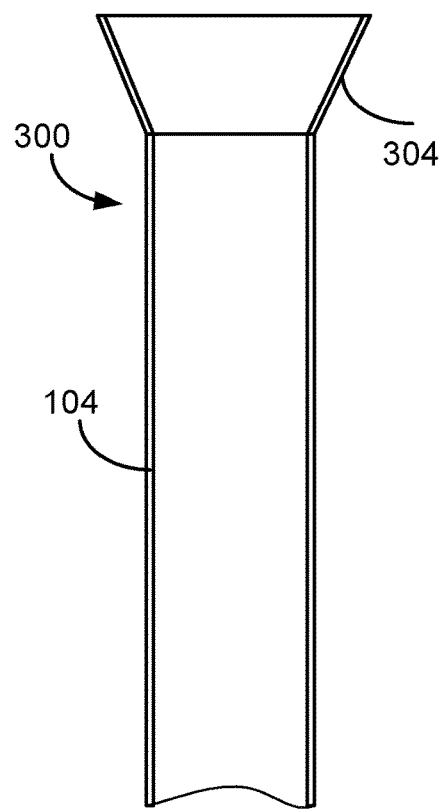
FIG. 2 Prior Art
FIG. 3 Prior Art

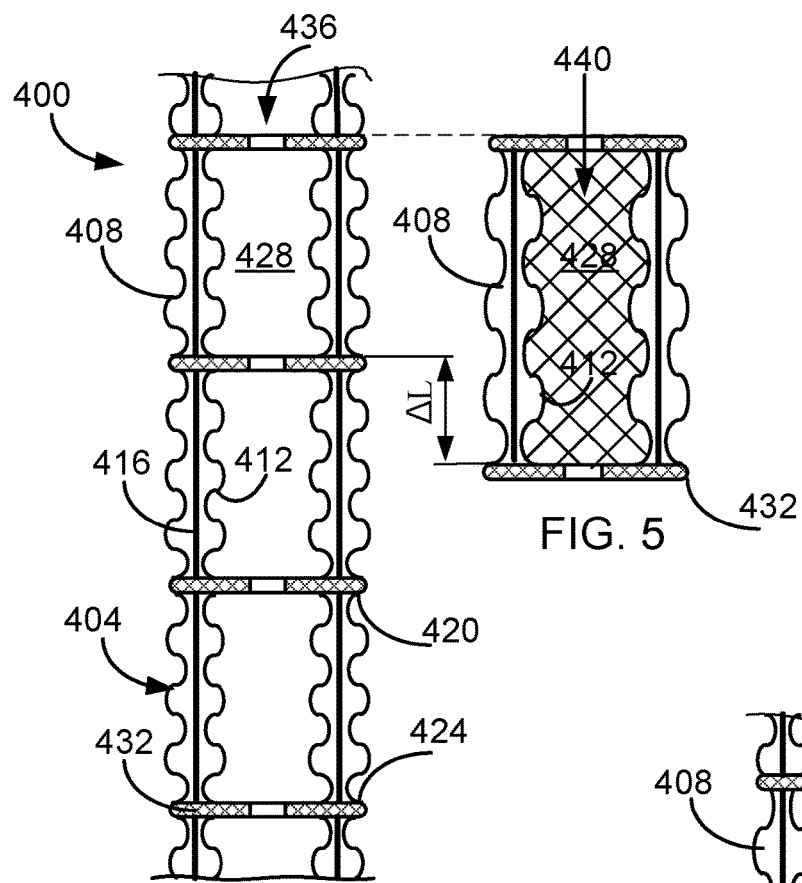
FIG. 4
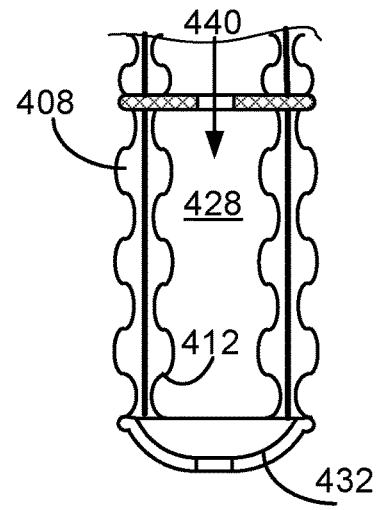
FIG. 5
FIG. 6

INTESTINAL SLEEVE

TECHNOLOGY FIELD

The present sleeve is related to sleeves for insertion into animal or human intestines.

BACKGROUND

Use of gastrointestinal implant devices and in particular bariatric devices is believed to be an effective treatment for obesity as well as for type 2 diabetes and a number of other obesity-related conditions. The bariatric devices are adapted to be inserted intraorally into the stomach and extend from the stomach into the intestines. All food exiting the stomach is funneled through the implant device.

A gastrointestinal implant device includes an unsupported flexible, collapsible sleeve and an anchor. The anchor is usually coupled to a proximal to the stomach portion of the sleeve. The flexible sleeve is open at both ends, and adapted to extend into the small intestine and in particular to duodenum to limit absorption of nutrients in the small intestine and duodenum. The anchor is adapted to secure and retain the sleeve within the duodenum.

Small intestine length being in contact with the digested food or chime determines the caloric absorptive capacity. The gastrointestinal implant device lining the intestine limits the small bowel length being in contact with the digested food. It receives from the stomach the digested food and delivers it 30-100 cm down the intestines. This delays the breakdown and subsequent digestion of food.

Different gastrointestinal devices including intestinal sleeves are described in several United States patents, including the following U.S. Pat. No. 8,855,770 to Gross et al.; U.S. Pat. No. 8,888,732 to Raven et al.; U.S. Pat. No. 8,956,380 to Dominguez et al.; U.S. Pat. No. 9,011,365 to Connor; U.S. Pat. No. 9,173,734 to Vargas; U.S. Pat. No. 9,289,580 to Coleman et al.; U.S. Pat. No. 9,463,107 to Babkes et al.; U.S. Pat. No. 9,504,591 to Burnett et al.; U.S. Pat. No. 9,681,974 to Dominguez et al.; U.S. Pat. No. 9,717,584 to Culley et al.; and United States Patent Application Publications 20030114803 to Lerner; 20120232459 to Dann et al.; 20140316265 to Levin et al. and 20170181877 to Binmoeller.

SUMMARY

An intestinal sleeve including one or more sleeve segments. Each sleeve segment is a coaxial structure that includes an outer cylindrical wall and an inner cylindrical wall and an elastic element disposed between the outer cylindrical wall and an inner cylindrical wall. The outer cylindrical wall and an inner cylindrical wall of the sleeve segment are furrow-like surfaces. A resilient membrane made from silicone is disposed between the sleeve segments and each resilient membrane includes a central opening. Each sleeve segment is configured to extend its length according to load carried by the resilient membrane and when the load is removed contract each sleeve segment to initial length.

Accordingly, presented also a method of extending length of an intestinal sleeve, such that the digested food entering the sleeve extends the length of the intestinal sleeve and extends the lining to a larger portion of the intestine. This reduces absorption of the digested food nutrients by the intestine.

LIST OF FIGURES AND THEIR BRIEF DESCRIPTION

FIG. 2 is an example of another prior art intestinal sleeve;

FIG. 3 is an example of an additional prior art intestinal sleeve;

FIG. 4 is an example of a present intestinal sleeve;

FIG. 5 is an example of a segment of the present sleeve;

FIG. 6 is another example of a segment of the present sleeve;

FIG. 8 is an example demonstrating how the present sleeve inserted into an intestine expands under a load; and.

DESCRIPTION

Gastrointestinal operations usually combine insertion of a restrictive gastric element anchored in a stomach and a certain extended tubular element residing in the intestines. The food is routed into the intestines and passes through the tubular element or sleeve. The sleeve is lining the internal walls of the intestines and causes certain effect of nutrients malabsorption. Generally, the sleeves are of constant length, although as disclosed in U.S. Pat. No. 7,682,330 the sleeve length could be variable and can range from about one foot to about five feet, when measured from the anchor. The patent does not disclose the means by which extension of sleeve length is achieved.

U.S. Pat. No. 9,289,580 discloses that the length of a sleeve can be adjusted in a variety of ways, for example, by rotating a rod disposed between the proximal and distal ends of the anastomotic device.

It is known that some suppliers of sleeves produce about three-four sizes adapted to physical parameters of the treated object. It is known that the sleeve length could be different for diabetes and weight reduction. However, a large number of obese people suffer also from diabetes.

It would be desirable to have a variable length sleeve that in course of its use could line/cover a variable length segment of the intestines.

Insertion of such sleeve would be a less invasive alternative to the bariatric surgery. The "active sleeve" that extends its length according to the amount of food ingested could improve both weight loss process and used for diabetes treatment.

Figure 1:
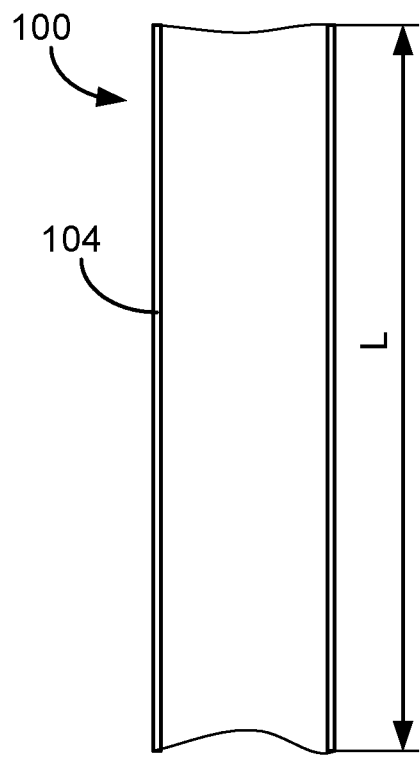
FIG. 1 is an example of a prior art intestinal sleeve.

FIGS. 1 through 3 illustrate different designs of currently manufactured intestinal sleeves. FIG. 1 is an example of a regular intestinal sleeve. Walls 104 of sleeve 100 are usually made from Tetrafluoroethylene or Polytetrafluoroethylene (PTFE) known under trade name Teflon®. Walls 104 could have a thickness of 20 to 50 micron. Sleeve 100 could be made of a desired length L, for example 50 or 60 cm. Teflon® is a material non-permeable by the chime and other products of stomach activity.

Sleeve 200 includes in one of its ends, typically the end proximal to stomach a longitudinal spring 204 configured to fix the sleeve to the intestine. The spring may reside in the stomach or be supported by the pylorus.

Sleeve 300 includes in one of its ends, typically the end proximal to stomach, a conical funnel like expansion 304 configured to fix the sleeve to the intestine. The funnel like expansion could reside in the stomach or be supported by the pylorus.

Generally, sleeves 100-300 in addition to their own supports are linked to supports or anchors residing in the stomach.

FIG. 4 is an example of a present intestinal sleeve 400. Intestinal sleeve 400 includes at least one sleeve segment 404 and usually a plurality of segments 404. The number of sleeve segments 404 sets the initial or original length of sleeve 400, although a single sleeve segment could be long enough and have a length similar to the existing sleeves length. Each sleeve segment 404 has a coaxial structure including an outer cylindrical wall 408 and an inner cylindrical wall 412. An elastic element 416 is disposed between walls 408 and 412 of each of the segments. Elastic element 416 could have a cylindrical shape or represent a number of separate elastic strips. The length of the elastic element 416 in a free, not tensioned state is generally shorter than the length of walls 408 and 412 of each of segments 404. This contracts the outer cylindrical wall 408 and inner cylindrical wall 412 such that their surface becomes a furrow-like surface forming on walls 408 and 412 structure of alternate protruding and recessing sections causing each segment 404 to look-like a bellow device, although the furrows shown as equally spaced, there spacing could be irregular. Bellows are devices the walls of which expand and contract in response to changes in the applied force. The applied force changes the length of the bellow.

Each sleeve segment 408 further comprises a first proximal to the stomach end 420, a second end 424, walls 408 and 412 and elastic element 416 that extends axially therebetween. Each end 420 and 424 of elastic element 416 is fixed to a respective resilient membrane 432. Wall 412 defines an interior chamber 428 that communicates with animal or human stomach. A resilient membrane 432 is attached to first 420 and second 424 ends. Resilient membrane 432 is disposed between segments 404 of intestinal sleeve 400 so as to divide the segments. Each resilient membrane 432 includes an opening 436 illustrated as a central opening, although opening 436 could be shifted from the center of resilient membrane 432. Resilient membrane 432 is typically made from silicone and has a thickness of 1.0 mm to 2.0 mm. The stiffness of resilient membrane could be regulated by using different thickness and type of silicone. In some examples resilient membrane 432 could be configured to bend under a load. Resilient membrane is configured to restore its initial position, when the load is removed. In some examples resilient membrane 432 could be made from the same material the sleeve is made and be integral with the sleeve.

Resilient membrane 432 receives load 440 (digested food or chime) from the stomach. As the load 440 is received and fills-in interior chamber 428, the force applied by load 440 to resilient membrane 432 as shown in FIG. 5, extends the lengths of segment 404 of intestinal sleeve 400 on a value of ΔL according to the load 440.

Each sleeve segment 408 extends under a load at least 5%. In some examples segment 408 extends 20% or even 50%. Accordingly, the length of intestinal sleeve 400 extends on the sum of extensions of each segment 408. When load 440 is removed, elastic element 416 is configured to contract each segment 408 to its' initial or original length.

Figure 7:
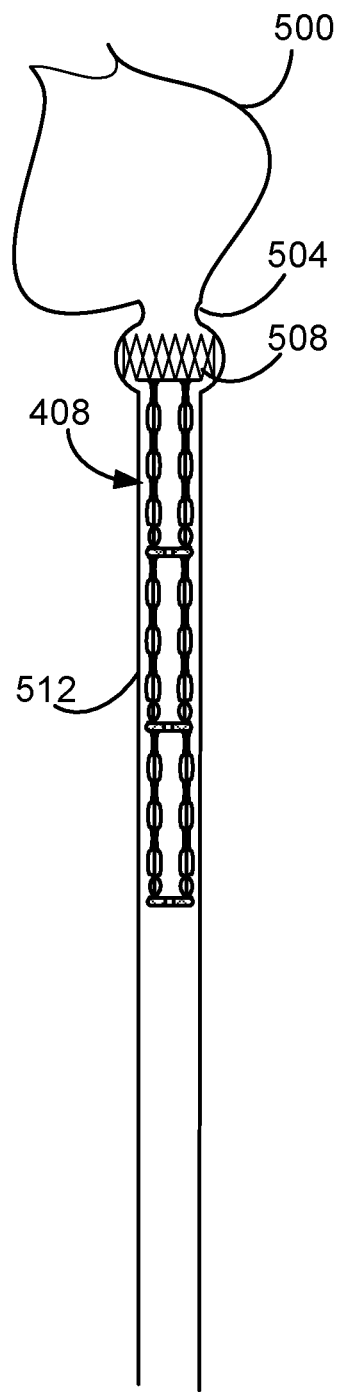
FIG. 7 is an example of the present sleeve inserted into an intestine.

FIG. 7 is an example of the present sleeve inserted into an intestine. The figure schematically illustrates stomach 500, pylorus 504 and an anchor such as longitudinal spring 508 holding or fixing in place inserted intraorally intestinal sleeve 400. Longitudinal spring 508 holds or fixes sleeve 400 at the entrance to the intestines. According to the present disclosure the insertion (placement) of a non-permeable intestinal sleeve 400 lining a segment of small intestine 512 leads to reduced nutrient absorption and helps in losing weight.

Figure 8:
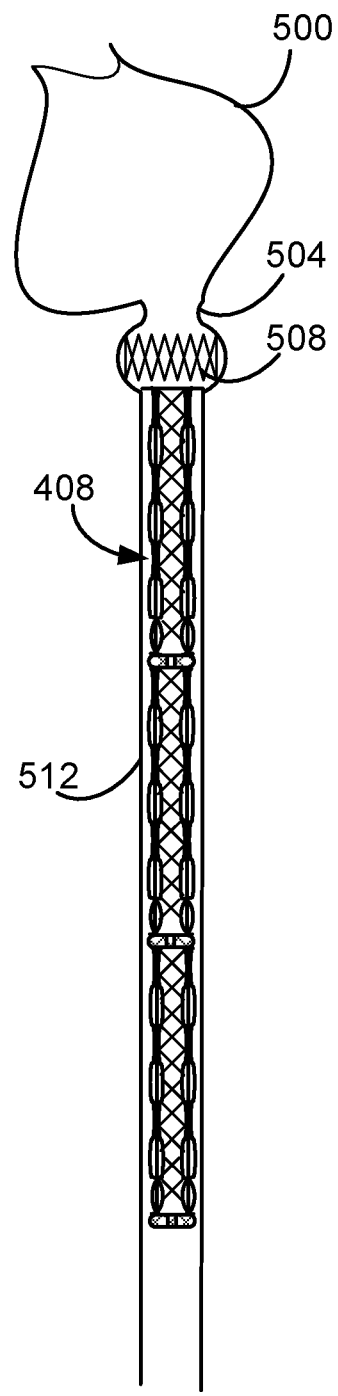

FIG. 8 is an example demonstrating how the present sleeve 408 inserted into an intestine extends its length under a load and increases the segment of small intestine 512 covered by the sleeve. The extended sleeve covers a longer segment of the small intestine walls and leads to reduced nutrient absorption helping to lose weight.

It is known that one of the obesity treatments includes insertion of a gastrointestinal system including an impermeable sleeve made from Teflon. The sleeve is anchored in the small intestine by a radially compressible nitinol wave anchor. The wave anchor anchors the sleeve and restrains the sleeve movement within the intestines.

The sleeve extends about 40-60 cm into the small intestine. This creates a mechanical barrier that allows food to bypass the duodenum and proximal jejunum without mixing with pancreas secretions. In addition to the spring anchors 508 restraining the movement from intestines into the stomach, the sleeve is anchored by an anchor residing in the stomach and restraining the movement of the sleeve down the intestines. U.S. Provisional Patent Application No. 62/613,065 to the same inventor and assignee and incorporated herein in its entirety discloses a bracelet type anchor that when inserted in the stomach 500 is restraining the movement of the sleeve down the intestines.

Figure 9:
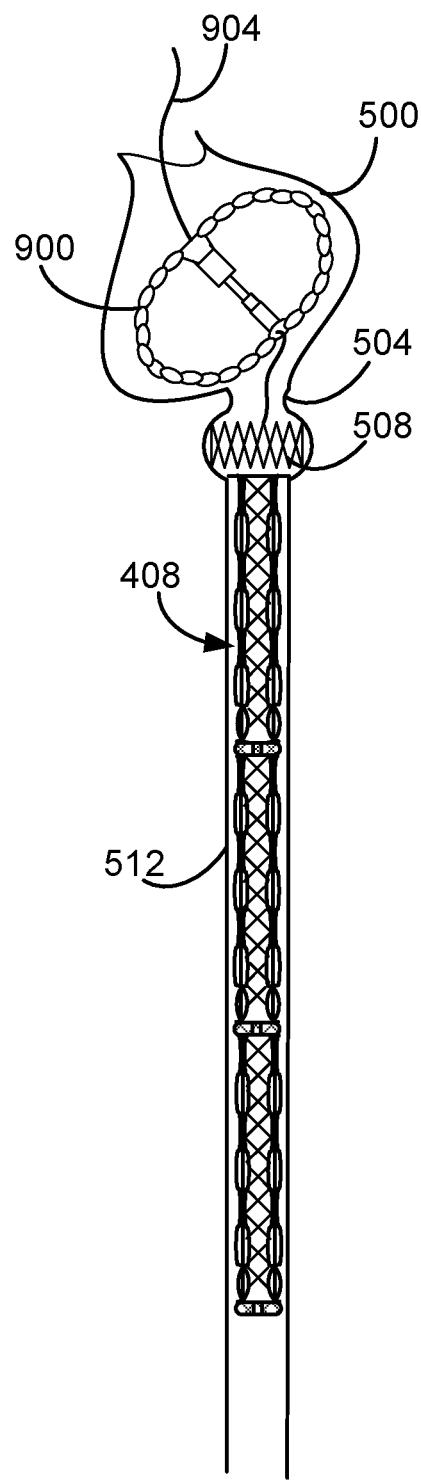
FIG. 9 is an example of a gastrointestinal system including an implantable bracelet type anchor and the disclosed above sleeve.

FIG. 9 is an example of a gastrointestinal system including an implantable bracelet type anchor and the disclosed above sleeve. The implantable bracelet type anchor or device 900 shown in the rigid state and fixed in body cavity which could be a stomach 500, when device 900 is in rigid state device 900 movement in body cavity 500 is constrained. String 904 links device 900 to wave anchor 508 and sleeve 408. String 904 is also used to lock the shape of bracelet type anchor 900. Bracelet type anchor 900 is inserted and removed from stomach 500 through standard intraoral procedures in a flexible mode. Pulling of string 904 transforms bracelet type anchor from the flexible mode into a rigid state.

A number of examples have been described. Nevertheless, it will be understood that various modifications may be made without departing from the spirit and scope of the method. Accordingly, other examples are within the scope of the following claims.

What is claimed is:

1. An intestinal sleeve, comprising:
   at least a pair of sleeve segments, each being a coaxial structure including an outer cylindrical wall and an inner cylindrical wall;
   an elastic element disposed between the outer cylindrical wall and an inner cylindrical wall; and
   a resilient membrane disposed between the segments,
   wherein the outer cylindrical wall and the inner cylindrical wall of the sleeve segment are furrow-like surfaces.

2. The sleeve according to claim 1, wherein each sleeve segment is configured to extend its length according to load.

3. The sleeve according to claim 1, wherein each sleeve segment extends under a load at least 5% of its length.

4. The sleeve according to claim 1, wherein each sleeve segment extends under a load at least 20% of its length.

5. The sleeve according to claim 1, wherein each sleeve segment extends under a load at least 50% of its length.

6. The sleeve according to claim 1, wherein the elastic element is configured to support extension of each sleeve segment when under load and when load is removed contract each sleeve segment to initial length.

7. The sleeve according to claim 1, wherein the resilient membrane includes a central opening.

8. The sleeve according to claim 1, wherein the resilient membrane is made from silicone.

9. The sleeve according to claim 1, wherein the resilient membrane is configured to bend under a load.

10. The sleeve according to claim 1, wherein the segments of the sleeve are made from Teflon.

11. The sleeve according to claim 1, wherein the elastic element located between two neighbor resilient membranes.

12. The sleeve according to claim 1, wherein each end of elastic element is fixed to a respective resilient membrane.

13. A method of extending length of an intestinal sleeve, comprising:
- inserting into intestines intraorally a sleeve including at least the pair of sleeve segments according to claim 1;
- fixing the sleeve at entrance to the intestines;
- digesting a certain amount of food sufficient to expand the sleeve to line a variable length of the intestine;
- limiting additional length of the intestine interacting with digested food; and
- when the digested food passes the intestinal sleeve retracting the sleeve to original length.

14. The method of claim 13 wherein the sleeve includes an elastic element supporting extension of each sleeve segment when under load and when load is removed, each sleeve segment contracts to its initial length.

15. A method of treating obesity by an intestinal sleeve, comprising:
- inserting intraorally into intestines a sleeve including at least one sleeve segment with extendable length according to claim 1;
- fixing the sleeve at entrance to the intestines;
- digesting a certain amount of food sufficient to expand the sleeve and form a lining of additional length of the intestine interacting with digested food; and
- when the digested food passes the intestinal sleeve retracting the sleeve to original length.

* * * * *